US00PP35248P2

(12) United States Plant Patent
Koot

(10) Patent No.: US PP35,248 P2
(45) Date of Patent: Jul. 4, 2023

(54) ***BEGONIA* PLANT NAMED 'DOBEGICBACRE'**

(50) Latin Name: *Begonia hybrida*
Varietal Denomination: Dobegicbacre

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/081,675

(22) Filed: Dec. 14, 2022

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./343
CPC ... A01H 5/02; A01H 5/00; A01H 6/18; A01H 6/185
See application file for complete search history.

(56) References Cited

PUBLICATIONS

PennState College of Agricultural Sciences FlowerTrials *Begonia* Beauvilia 'Red', retrieved on Feb. 22, 2023 at https://agsci.psu.edu/flower-trials/trial-year/2022/plant-name/begonia-beauvilia-red, 2 pp. (Year: 2023).*
Trademark Electronic Search System (TESS) for Beauvilia, retrieved on Feb. 22, 2023 at https://tmsearch.uspto.gov/bin/showfield?f=doc&state=4802:e5hidt.2.1, 2 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Begonia* plant named 'Dobegicbacre', characterized by its relatively compact, semi-upright to trailing and mounded plant habit; moderately vigorous growth habit; freely basal branching habit; dark green-colored leaves; freely and continuously flowering habit; and single flowers that are bright red in color.

1 Drawing Sheet

Botanical designation: *Begonia hybrida.*
Cultivar denomination: 'DOBEGICBACRE'.

BACKGROUND OF THE INVENTION

The present invention relates to a new and distinct cultivar of *Begonia* plant, botanically known as *Begonia hybrida*, and hereinafter referred to by the name 'Dobegicbacre'.

The new *Begonia* plant is a product of a planned breeding program conducted by the Inventor in De Lier, The Netherlands. The objective of the breeding program was to develop new compact, freely branching and freely flowering *Begonia* plants with large and attractive flowers.

The new *Begonia* plant originated from a cross-pollination made by the Inventor during the autumn of 2016 of a proprietary selection of *Begonia hybrida* identified as code number BG13-000502-001, not patented, as the female, or seed, parent with a proprietary selection of *Begonia hybrida* identified as code number BG-5862, not patented, as the male, or pollen, parent. The new *Begonia* plant was discovered and selected by the Inventor as a single flowering plant from within the progeny of the stated cross-pollination in a controlled greenhouse environment in De Lier, The Netherlands during the spring of 2017.

Asexual reproduction of the new *Begonia* plant by vegetative tip cuttings in a controlled greenhouse environment in De Lier, The Netherlands since the spring of 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobegicbacre'. These characteristics in combination distinguish 'Dobegicbacre' as a new and distinct *Begonia* plant:

1. Relatively compact, semi-upright to trailing and mounded plant habit.
2. Moderately vigorous growth habit.
3. Freely basal branching habit.
4. Dark green-colored leaves.
5. Freely and continuously flowering habit.
6. Single flowers that are bright red in color.

Plants of the new *Begonia* can be compared to plants of the female parent selection. In side-by-side comparisons, plants of the new *Begonia* differ primarily from plants of the female parent selection in the following characteristics:

1. Plants of the new *Begonia* are more trailing than and not as upright as plants of the female parent selection.
2. Plants of the new *Begonia* flower earlier than plants of the female parent selection.
3. Plants of the new *Begonia* have bright red-colored flowers whereas plants of the female parent selection have orangish red-colored flowers.

Plants of the new *Begonia* can be compared to plants of the male parent selection. In side-by-side comparisons, plants of the new *Begonia* differ primarily from plants of the male parent selection in the following characteristics:

1. Plants of the new *Begonia* are denser than and not as open as plants of the male parent selection.
2. Plants of the new *Begonia* have shorter internodes than plants of the male parent selection.
3. Plants of the new *Begonia* have dark green-colored leaves whereas plants of the male parent selection have dark brownish green-colored leaves.

Plants of the new *Begonia* can be compared to plants of *Begonia hybrida* BEAUVILIA 'Red', not patented. In side-by-side comparisons, plants of the new *Begonia* differ primarily from plants of BEAUVILIA 'Red' in the following characteristics:

1. Plants of the new *Begonia* are more compact than plants of BEAUVILIA 'Red'.
2. Plants of the new *Begonia* are not as vigorous as plants of BEAUVILIA 'Red'.
3. Plants of the new *Begonia* are more freely branching than plants of BEAUVILIA 'Red'.
4. Plants of the new *Begonia* have shorter internodes than plants of BEAUVILIA 'Red'.
5. The lower leaf surfaces of plants of the new *Begonia* are purplish red in color whereas the lower leaf surfaces of plants of BEAUVILIA 'Red' are green in color.
6. Flowers of plants of the new *Begonia* are lighter red in color than flowers of plants of BEAUVILIA 'Red'.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant.

The photograph is a side perspective view of a typical flowering plant of 'Dobegicbacre' grown in a container.

DETAILED BOTANICAL DESCRIPTION

Plants used for the aforementioned photograph and following observations and measurements were grown in 12-cm containers during the summer in a glass-covered greenhouse in De Lier, The Netherlands. During the production of the plants, day temperatures ranged from 20° C. to 35° C., night temperatures ranged from 17° C. to 25° C. and minimum light level was 135 watt/m$^2$. Plants were 13 weeks old when the photograph was taken and twelve weeks old when the description was taken. In the following description, color references are made to The Royal Horticultural Society Colour Chart, Fifth Edition, except where general terms of ordinary dictionary significance are used.

Botanical classification: *Begonia hybrida* 'Dobegicbacre'.

Parentage:

*Female, or seed, parent*.—Proprietary selection of *Begonia hybrida* identified as code number BG13-000502-001, not patented.

*Male, or pollen, parent*.—Proprietary selection of *Begonia hybrida* identified as code number BG-5862, not patented.

Propagation:

*Type*.—By vegetative tip cuttings.

*Time to initiate roots, summer*.—About 18 days at temperatures about 22° C. to 30° C.

*Time to initiate roots, winter*.—About 21 days at temperatures about 20° C. to 22° C.

*Time to produce a rooted young plant, summer*.—About 22 to 25 days at temperatures about 22° C. to 30° C.

*Time to produce a rooted young plant, winter*.—About 25 to 28 days at temperatures about 20° C. to 22° C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Semi-upright to trailing and mounded plant habit; relatively compact; becoming more pendulous with development; freely basal branching with about three primary lateral branches each with about three to four secondary lateral branches; moderately vigorous growth habit and moderate growth rate.

*Plant height*.—About 11 cm.

*Plant width*.—About 36 cm.

*Lateral branch description*.—Length: About 10.5 cm. Diameter: About 8 mm. Internode length: About 2 cm. Texture and luster: Pubescent; semi-glossy. Aspect: Semi-upright to trailing. Strength: Moderately strong, flexible. Color, developing: Close to 152C. Color, developed: Close to 152B.

*Leaf description*.—Arrangement: Alternate, simple. Length: About 9 cm. Width: About 3.8 cm. Shape: Lanceolate. Apex: Narrowly acute. Base: Oblique. Margin: Senate; sinuses medium in depth and divergent. Texture and luster, upper and lower surfaces: Pubescent; semi-glossy. Venation pattern: Palmate; reticulate. Color: Developing and fully expanded leaves, upper surface: Close to 139A; venation, close to 144C. Developing and fully expanded leaves, lower surface: Close to 71A; venation, close to 146C. Petioles: Length: About 3 cm. Diameter: About 3 mm. Texture and luster, upper and lower surfaces: Smooth, glabrous; semi-glossy. Strength: Moderately strong; flexible. Color, upper surface: Close to 148B to 148C. Color, lower surface: Close to 148B.

Flower description:

*Flowering habit*.—Single flowers arranged in axillary cymes; freely flowering habit with typically about three flowers per inflorescence and about 48 open flowers and flower buds per plant at one time; flowers are mostly nodding.

*Fragrance*.—None detected.

*Natural flowering season*.—Plants begin flowering about eight weeks after planting; long flowering period, in the garden plants flower freely and continuously from the late spring throughout the summer in Northern Europe and can be flowered year-round in greenhouses.

*Flower longevity*.—Individual flowers last about four weeks on the plant; flowers not persistent.

*Inflorescence height*.—About 5 cm.

*Inflorescence diameter*.—About 7 cm.

*Flower buds*.—Length: About 2.2 cm. Diameter: About 1.8 cm. Shape: Ovoid. Texture and luster: Smooth, glabrous; semi-glossy. Color: Close to 42A.

*Flower size*.—Diameter: About 2 cm by 2.4 cm. Depth (height): About 2.5 cm.

*Flower petals*.—Quantity per flower and arrangement: Typically four to five per flower arranged in a single whorl; petals imbricate. Length: About 2.5 cm. Width: About 1.8 cm. Shape: Obovate. Apex: Rounded and emarginate. Base: Cuneate and truncate. Margin: Entire. Texture and luster, upper surface: Smooth, glabrous; matte. Texture and luster, lower surface: Smooth, glabrous; semi-glossy. Color: When opening and fully opened, upper surface: Close to 44A; venation, close to 44A; color does not change with subsequent development. When opening and fully opened, lower surface: Close to 44A; venation, close to 44A; color does not change with subsequent development.

*Flower sepals*.—Quantity per flower and arrangement: Typically four or five per flower arranged in a single whorl. Length: About 2.5 cm. Width: About 1.2 cm. Shape: Obovate. Apex: Rounded and emarginate. Base: Obtuse. Margin: Entire. Texture and luster, upper and lower surfaces: Smooth, glabrous; semi-glossy. Color: When opening and fully opened, upper surface: Close to 44A. When opening and fully opened, lower surface: Close to 44A.

*Flower peduncles*.—Length: About 4.5 cm. Diameter: About 4 mm. Aspect: Semi-trailing. Strength: Moderately strong; flexible. Texture and luster: Smooth, glabrous; glossy. Color: Close to 152C.

*Flower pedicels*.—Length: About 1.2 cm. Diameter: About 2 mm. Aspect: Outwardly to semi-trailing. Strength: Moderately strong. Texture and luster: Smooth, glabrous; glossy. Color: Close to 59D.

*Reproductive organs*.—Stamens: Quantity of stamens per flower: About three. Filament length: About 4 mm. Filament color: Close to 28B. Anther length: About 4 mm. Anther shape: Oval. Anther color: Close to 13A. Amount of pollen: Moderate. Pollen color: Close to 13A. Pistils: Quantity of pistils per flower: Three. Pistil length: About 4 mm. Style length: About 3.5 mm. Style color: Close to 34A. Stigma diameter: About 4 mm. Stigma shape: Curled, bi-lobed. Stigma color: Close to 34A. Ovary color: Close to 145B. Fruits and seeds: To date, fruit and seed development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate temperatures ranging from about 10° C. to about 35° C.

It is claimed:

1. A new and distinct *Begonia* plant named 'Dobegicbacre' as illustrated and described.

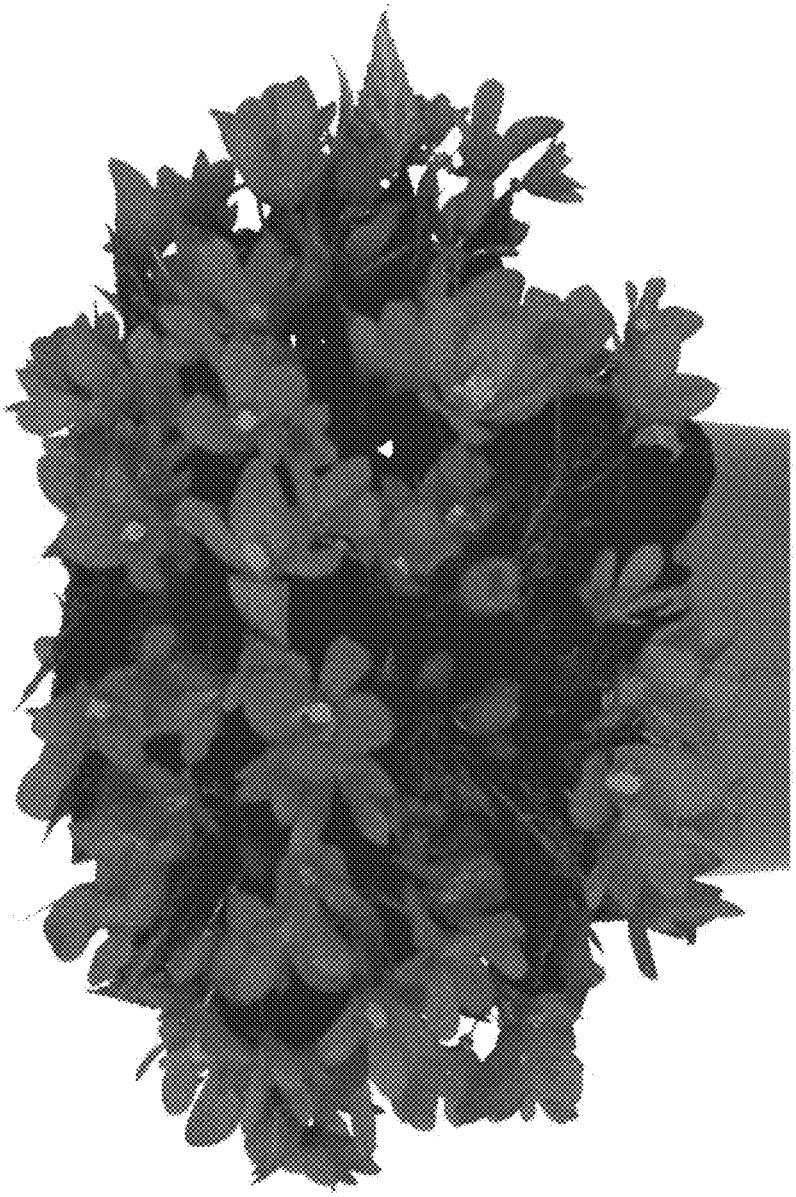

* * * * *